United States Patent
Sughrue et al.

(10) Patent No.: US 11,848,098 B2
(45) Date of Patent: *Dec. 19, 2023

(54) IDENTIFYING ANOMALOUS BRAIN DATA

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 13 days.

This patent is subject to a terminal disclaimer.

(21) Appl. No.: 17/373,637

(22) Filed: Jul. 12, 2021

(65) Prior Publication Data
US 2022/0005600 A1    Jan. 6, 2022

Related U.S. Application Data

(63) Continuation of application No. 16/920,078, filed on Jul. 2, 2020, now Pat. No. 11,087,877.

(51) Int. Cl.
*G16H 40/63* (2018.01)
*G16H 30/20* (2018.01)

(52) U.S. Cl.
CPC .............. *G16H 40/63* (2018.01); *G16H 30/20* (2018.01)

(58) Field of Classification Search
CPC ................................ G16H 40/63; G16H 30/20
(Continued)

(56) References Cited

U.S. PATENT DOCUMENTS 10,255,675 B2    4/2019   Sakaue et al.
2004/0092809 A1*   5/2004   DeCharms ........... A61B 5/0042
                                                     600/410
(Continued)

FOREIGN PATENT DOCUMENTS

KR    10-2019-0028901    3/2019

OTHER PUBLICATIONS

Ru, Kong; Individual-Specific Network-Level and Areal-Level Parcellations of the Human Cerebral Cortex; National University of Singapore (Singapore). ProQuest Dissertations Publishing, 2018. 13855498. (Year: 2018).*

(Continued)

*Primary Examiner* — Hiep V Nguyen
(74) *Attorney, Agent, or Firm* — Fish & Richardson P.C.

(57) ABSTRACT

Methods, systems, and apparatus, including computer programs encoded on computer storage media, for determining anomalous brain data. One of the methods includes obtaining brain data characterizing brain activity of a patient; for each of a plurality of pairs of parcellations comprising a first parcellation and a second parcellation, processing the brain data to generate a correlation between the brain activity of the first and second parcellations; obtaining second connectivity data that characterizes, for each of the plurality of pairs of parcellations, a normal range of correlations between the brain activity of the first and second parcellations; identifying one or more of the plurality of pairs of parcellations for which the correlation between brain activity of the first and second parcellations is outside of the corresponding normal range of correlations; and providing data characterizing the one or more identified pairs of parcellations for display to a user on a graphical interface.

21 Claims, 7 Drawing Sheets

(58) Field of Classification Search
USPC .......................................................... 705/2
See application file for complete search history.

(56) References Cited

U.S. PATENT DOCUMENTS

2016/0063701 A1* 3/2016 Chen .................. G06F 2218/22
382/128
2018/0314691 A1 11/2018 Mori et al.

OTHER PUBLICATIONS

[No Author Listed], "Connectivity Matrices and Brain Graphs" Fundamentals of Brain Network Analysis, 2016, 89-113.

Becker et al., "Going Beyond Diffusion Tensor Imaging Tractography in Eloquent Glioma Surgery—High-Resolution Fiber Tractography: Q-Ball or Constrained Spherical Deconvolution?" World Neurosurg., Feb. 2020 134:e596-609.

Bonney et al., A Simplified Method of Accurate Postprocessing of Diffusion Tensor Imaging for Use in Brain Tumor Resection. Oper Neurosurg (Hagerstown) 13, 47-59 (2017).

Burks et al., "A method for safely resecting anterior butterfly gliomas: the surgical anatomy of the default mode network and the relevance of its preservation". J. Neurosurg., Sep. 2016, 126(6):1795-811.

Dell'Acqua and Tournier, "Modelling white matter with spherical deconvolution: How and why?" NMR Biomed., 2019, 32:e3945.

Faber et al., "Critical elements for connectivity analysis of brain networks" Universidade Federal de São Paulo—UNIFESP, 2019, 39 pages.

Fan et al., "The Human Brainnetome Atlas: A New Brain Atlas Based on Connectional Architecture," Cereb Cortex, 2016, 26:3508-26.

Fischl, "FreeSurfer," Neuroimage, 2012, 62:774-81.

Garyfallidis et al., "Dipy, a library for the analysis of diffusion MRI data," Frontiers in Neuroinformatics, 2014, 8:1-17.

Glasser et al., "A multi-modal parcellation of human cerebral cortex," Nature, 2016, 536:171-8.

Glenn et al., "Common Disconnections in Glioma Surgery: An Anatomic Description," Cureus, 2017, 9:e1778.

Horwitz et al., "Interpreting the Effects of Altered Brain Anatomical Connectivity on fMRI Functional Connectivity: A Role for Computational NeuralModeling," Frontiers in Human Neurosci., Nov. 2013, 7:649.

Ille et al., Functional Reorganization of Cortical Language Function in Glioma Patients—A Preliminary Study. Frontiers in Oncology 9 (2019), 9(446):1-8.

International Search Report and Written Opinion in International Appln. No. PCT/AU2021/050684, dated Oct. 8, 2021, 17 pages.

Jin et al., "Functional and anatomical connectivity-based parcellation of human cingulate cortex." Brain Behav., 2018, 8:e01070.

Ohue et al., "Evaluation of intraoperative brain shift using an ultrasound-linked navigation system for brain tumor surgery," Neurol. Med. Chir., 2010, 50:291-300.

Panesar et al., "Tractography for Surgical Neuro-Oncology Planning: Towards a Gold Standard," Neurotherapeutics, 2019, 16:36-51.

Rijnen et al., "Cognitive functioning in patients with low-grade glioma: effects of hemispheric tumor location and surgical procedure" 2019, 1(4):81-99.

Shagun Ajmera, Decoding Task-Specific Cognitive States with Slow, Directed Functional Networks in the Human Brain, https://doi.org/10.1523/ENEURO.0512-19.2019, Jul./Aug. 2020 7(4) ENEURO.0512-19.2019 1-23 (Year: 2020).

Smitha et al., "Resting state fMRI: A review on methods in resting state connectivity analysis and resting state networks," Neuroradiol. J., 2017, 30:305-17.

* cited by examiner

IDENTIFYING ANOMALOUS BRAIN DATA

CROSS-REFERENCE TO RELATED APPLICATION

This application is a continuation of and claims priority to U.S. patent application Ser. No. 16/920,078, filed Jul. 2, 2020, the entire contents of which are incorporated herein by reference.

BACKGROUND

This specification relates to processing data related to the brain of a patient, e.g., functional magnetic resonance imaging (MRI) data and/or tractography data.

Brain functional connectivity data characterizes, for each of one or more pairs of locations within the brain of a patient, the degree to which brain activity in the pair of locations is correlated.

One can gather data related to the brain of the patient by obtaining and processing images of the brain of the patient, e.g., using magnetic resonance imaging (MRI), diffusion tensor imaging (DTI), or functional MRI imaging (fMRI). Diffusion tensor imaging uses magnetic resonance images to measure diffusion of water in a human brain. One can use the measured diffusion to generate tractography data, which can include images of neural tracts and corresponding white matter fibers of the subject brain.

Data related to the brain of a single patient can be highly complex and high-dimensional, and therefore difficult for a clinician to manually inspect and parse, e.g., to plan a surgery or diagnose the patient for a brain disease or mental disorder. For example, a correlation matrix, e.g., a correlation matrix of fMRI data, of the brain of a patient can be a matrix with hundreds of thousands or millions of elements.

SUMMARY

This specification relates to determining a subset of brain data of a patient that is anomalous, i.e., a subset of brain data of the patient that is outside a normal range, e.g., as defined by the brain data of other patients. The system can then display data corresponding to the determined subset of the brain data to a user for further inspection.

In this specification, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., correlation matrices.

Particular embodiments of the subject matter described in this specification can be implemented so as to realize one or more of the following advantages. As discussed above, a set of brain data characterizing the brain of a single patient can often be incredibly large and complicated, and thus it can be difficult and time consuming for a user to extract useful information from the set of brain data. Using techniques described in this specification, a system can quickly identify one or more pairs of parcellations whose correlation is outside a normal range, and therefore might be an indicator of a brain disease. The system can then display data characterizing the identified pairs of parcellations to the user, so that the user is not forced to search through and analyze a large amount of data that is not clinically relevant. Therefore, the amount of time that a user must spend to discover the portion of the brain data that is useful to the user can be drastically reduced, resulting in improved outcomes for patients, users and/or clinicians, especially when effective care requires time sensitive investigations.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can determine a subset of brain data of a patient that is anomalous. In this specification, a set of brain data is "anomalous" if the values of the brain data are outside a predetermined normal range of values, e.g., as defined by a data set that includes brain data corresponding to multiple other patients.

Figure 1A:
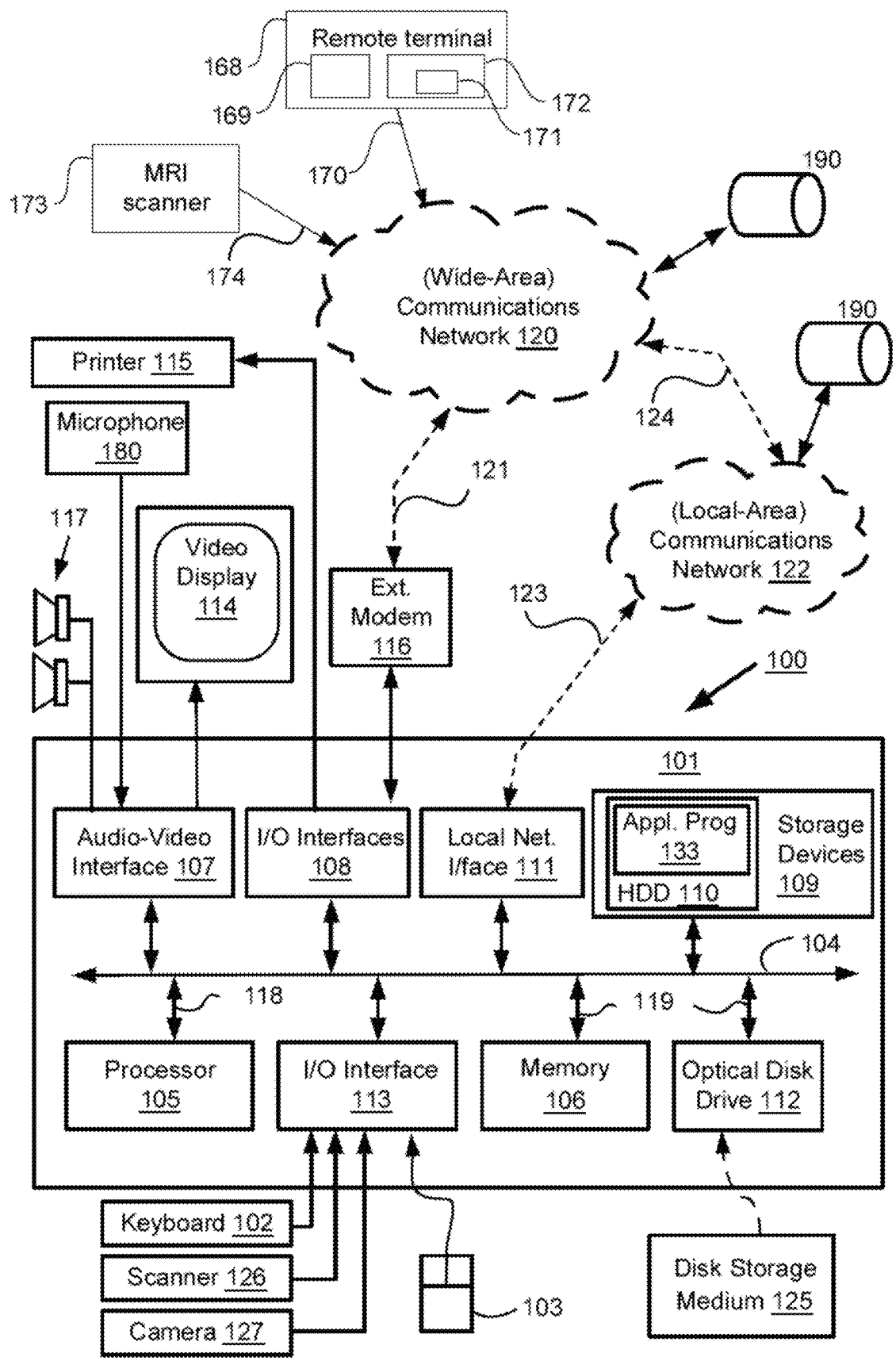
FIG. 1A and FIG. 1B are block diagrams that illustrate an example computer system for use in processing medical images.
Figure 1B:
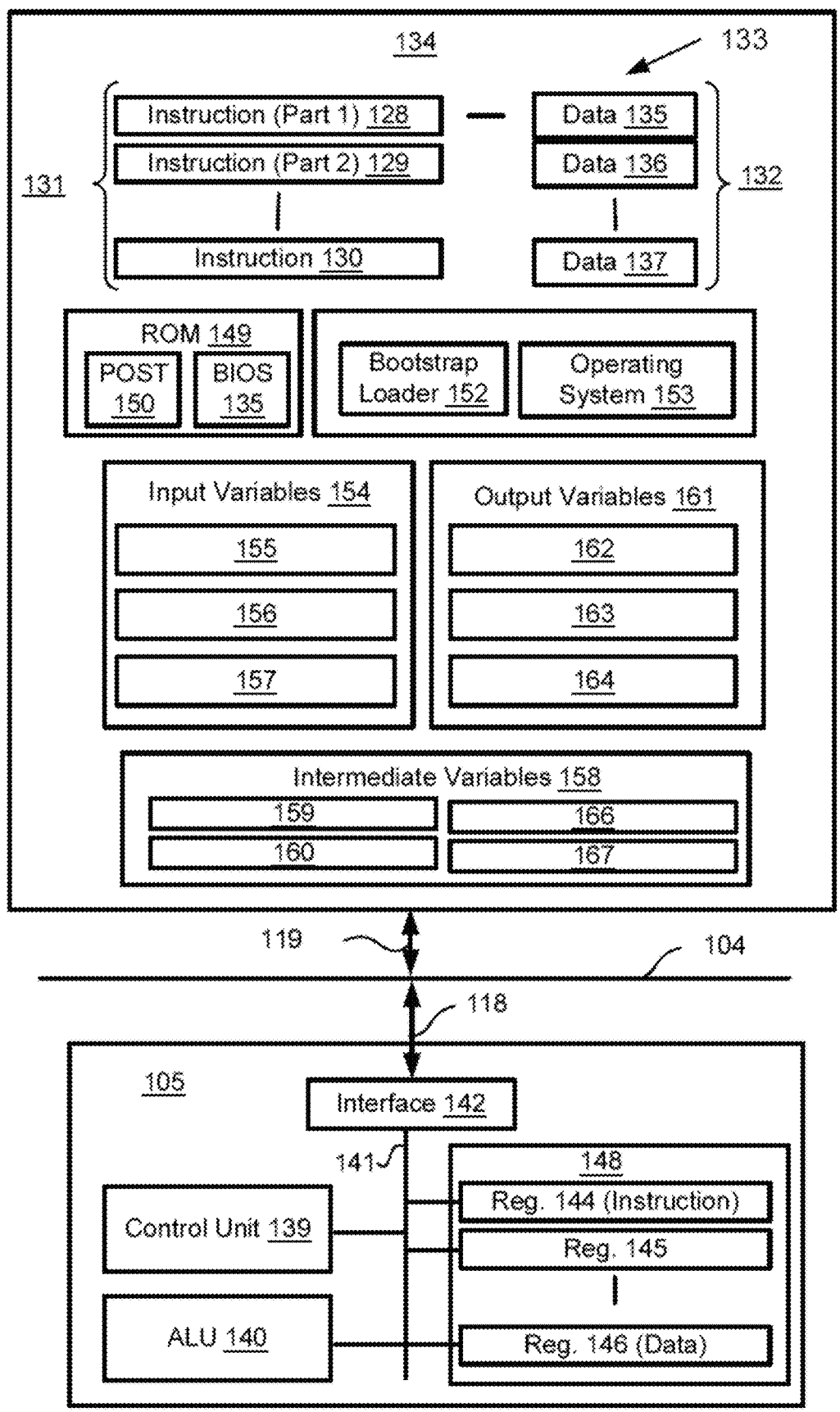

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such as an MRI or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2A:
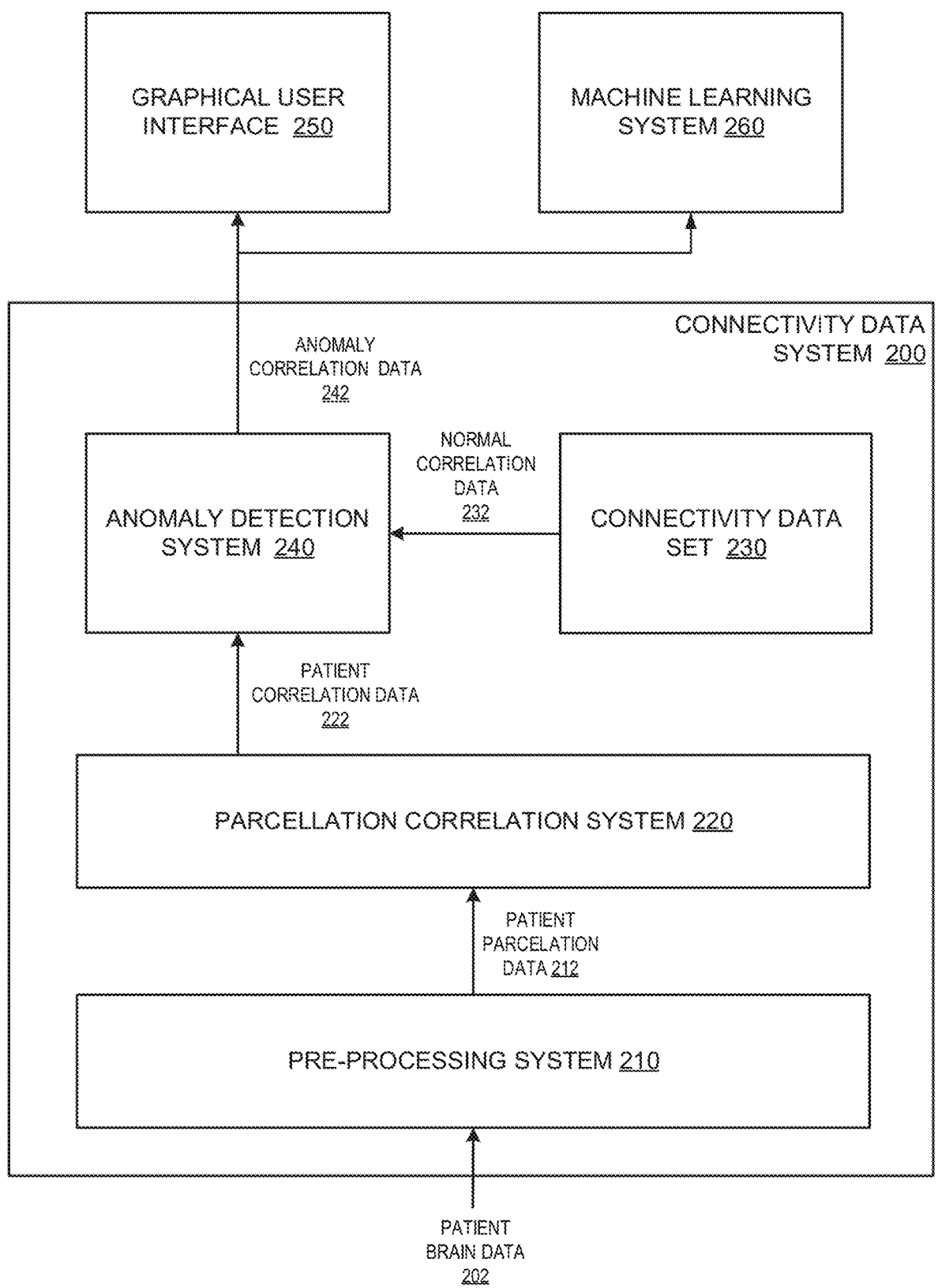
FIG. 2A and FIG. 2B are diagrams of an example connectivity data system.
Figure 2B:
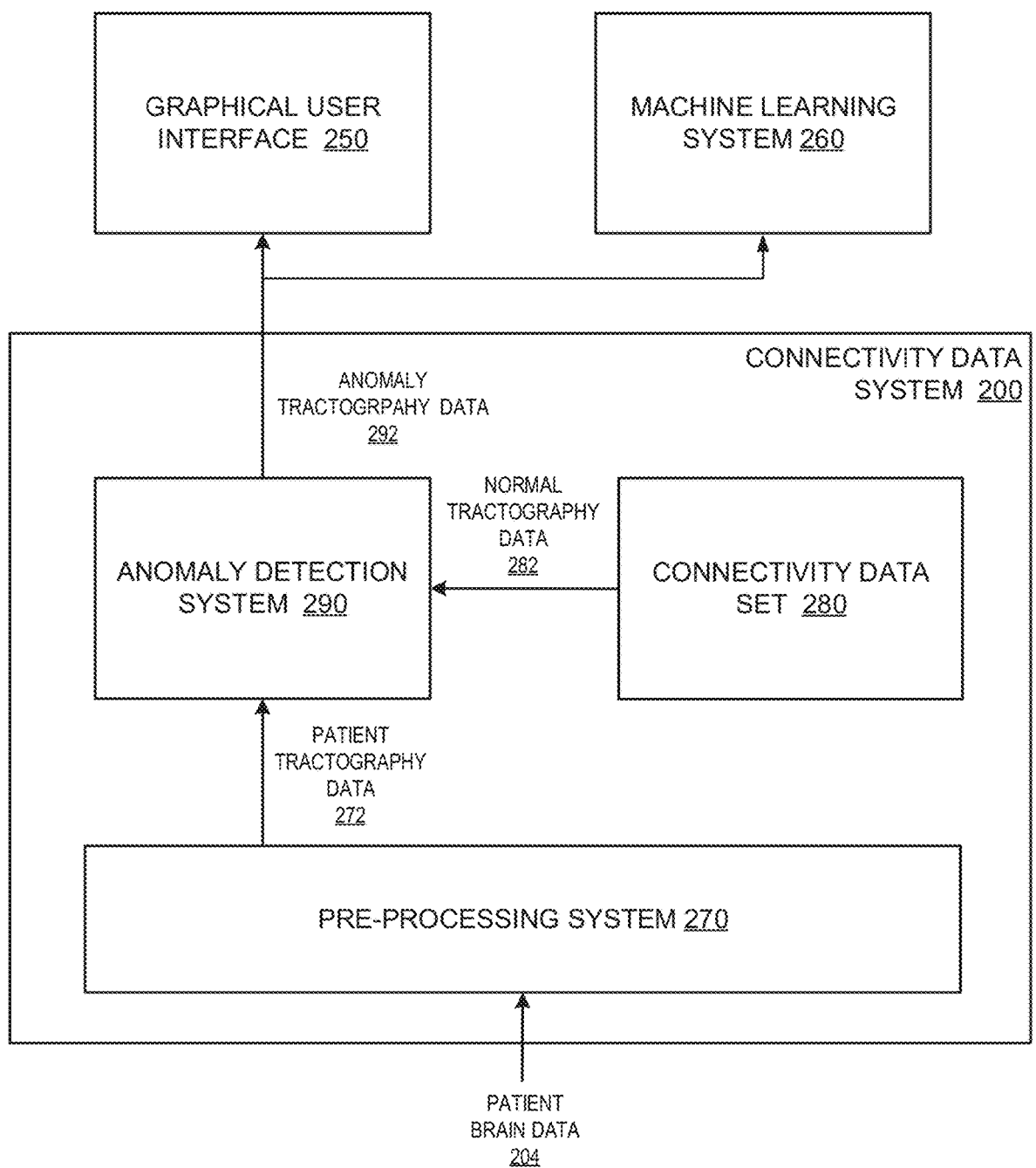

FIG. 2A and FIG. 2B are diagrams of example connectivity data system 200 and 201, respectively. The connectivity data systems 200 and 201 are examples of systems implemented as computer programs on one or more computers in one or more locations, in which the systems, components, and techniques described below can be implemented. As depicted in FIG. 2A, the connectivity data system 200 is configured to determine one or more anomalies in correlation data characterizing the correlation between the brain activity of different pairs of parcellations in the brain of the patient. As depicted in FIG. 2B, the connectivity data system 201 is configured to determine one or more anomalies in tractography data characterizing a number of tracts connecting different pairs of parcellations in the brain of the patient.

Referring to FIG. 2A, the connectivity data system 200 is configured to obtain patient brain data 202 characterizing the brain of a patient and process the patient brain data 202 to generate anomaly correlation data 242, which identifies one or more regions of the brain of the patient for which the patient brain data 202 was anomalous. For example, the patient brain data 202 can include one or more of blood-oxygen-level-dependent imaging data, fMRI data, or EEG data captured from the brain of the patient.

The connectivity data system 200 includes a pre-processing system 210, a parcellation correlation system 220, a connectivity data set 230, and an anomaly detection system 240.

The pre-processing system 210 is configured to obtain the patient brain data 202 and process the patient brain data 202 to generate patient parcellation data 212 which organizes the patient brain data 202 according to multiple different parcellations of the brain of the patient.

For example, the patient brain data 202 can include multiple different time series characterizing the activity of a respective different region of the brain of the patient over time, e.g., a time series corresponding to each three-dimensional voxel of the brain that can be measured by an MRI machine. The pre-processing system 210 can organize the different time series signals by parcellation according to a brain atlas of the brain. The pre-processing system can then, for each parcellation, combine the different time series signals corresponding to the parcellation, e.g., by determining an average of the different time series signals In this specification, a brain atlas is data that defines one or more parcellations of a brain of a patient, e.g., by defining in a common three-dimensional coordinate system the coordinates of the outline of the parcellation or the volume of the parcellation.

In some implementations the pre-processing system 210 performs one or more additional pre-processing steps to generate the patient parcellation data 212. For example, the pre-processing system 210 can perform smoothing on the patient brain data 202, e.g., to remove components of the patient brain data 202 that are not clinically relevant such as brain activity data related to the heartbeat or breathing of the patient. As another example, the pre-processing system 210 can perform skull stripping on the patient brain data 202. As another example, the pre-processing system 210 can remove one or more slices in brain data 202 in order to allow for signal stabilization. As another example, the pre-processing system 210 can perform slice timing correction on the brain data 202. As another example, the pre-processing system 210 can perform motion correction on the brain data 202. As another example, the pre-processing system 210 can perform gradient distortion correction on the brain data 202. As another example, the pre-processing system 210 can perform global intensity normalization on the brain data 202. As another example, the pre-processing system 210 can calculate one or more confounds using the brain data 202. As another example, the pre-processing system 210 can apply a whitening transform to the brain data 202.

The parcellation correlation system 220 is configured to obtain the patient parcellation data 212 and to process the patient parcellation data 212 to generate patient correlation data 222 that characterizes, for each pair of parcellation of the multiple parcellations in the patient parcellation data 212, a correlation between brain activity of the first parcellation and brain activity of the second parcellation in the brain of the patient.

For example, the patient parcellation data 212 can include one or more time series signals corresponding to each parcellation, and the parcellation correlation system 220 can determine, for each pair of parcellations, a correlation between the vales of the time series of the first parcellation and the time series of the second parcellation.

The anomaly detection system 240 is configured to obtain the patient correlation data 222 and to process the patient correlation data 222 to generate the anomaly correlation data 242. The anomaly correlation data 242 identifies one or more pairs of parcellations whose correlation in the patient correlation data 222 is anomalous.

In some implementations, the anomaly detection system 240 determines the anomaly correlation data 242 by processing the patient correlation data 222 using a machine learning model that is configured to process correlation data and identity one or more pairs of parcellations that are anomalous. For example, the machine learning model can be trained using correlation data obtained from the respective brain of multiple other patients, e.g., training data stored in the connectivity data set 230.

In some other implementations, the anomaly detection system 240 can determine the one or more anomalous pairs of parcellations according to normal correlation data 232 obtained from the connectivity data set 230. In some implementations, the normal correlation data 232 identifies, for each pair of parcellations in the patient parcellation data 222, a range of values for the correlation between the pair of parcellations that is considered "normal." The normal range can be determined by the connectivity data set 230 according to the correlation between the pair of parcellations measured in the respective brain of multiple other patients. For example, the normal correlation data 232 can be determined from brain data captured from hundreds, thousands, or millions of other patients. As a particular example, the normal correlation data 232 might identify, for each pair of parcellations, an average correlation between the pair of parcellations and a standard deviation of correlations between the pair of parcellations, as determined from the correlations measured in the brains of the other patients.

The anomaly detection system 240 uses the normal correlation data 232 to determine the one or more anomalous pairs of parcellations in the brain of the patient in the anomaly correlation data 242. As a particular example, the anomaly detection system 240 might determine that the correlation between a pair of parcellations is anomalous if the correlation is outside a range of values defined by the average correlation and standard deviation of correlations of the pair of parcellations. For example, the correlation between a pair of parcellations may be anomalous if it is outside one, two, three, or four standard deviations of the average correlation.

As another particular example, the anomaly detection system 240 might determine that a set of two or more pairs of parcellations are anomalous only if each of the pairs in the set of pairs of parcellations is outside of a normal range of values for the set of pairs of parcellations. That is, the anomaly detection system 240 might maintain data that identifies sets of multiple pairs of parcellations that are related to each other, e.g., that are each related to the same disease, such that the anomaly detection system 240 should only determine that an anomaly has occurred if each pair of parcellations in the set of parcellations is anomalous. In this example, normal correlation data 232 might identify a range of normal correlation values corresponding to each pair in the set of pairs of parcellations, where the range of normal correlation values of a first pair in the set depends on the correlation value of one or more other pairs in the set. For example, for any combination of correlation values for the other pairs in the set, the normal correlation data 232 might define a particular normal range of correlation values for the first pair.

In some implementations, the anomaly detection system 240 might identify one or more pairs of parcellations whose "normal" correlations, as identified in the normal correlation data 232, are too variable or too unpredictable to draw a conclusion about the corresponding correlation identified in the patient correlation data 222. For example, the anomaly detection system 240 might determine that the correlations between a pair of parcellations is too variable if the standard deviation or variance of the correlations of the pair of parcellations, as identified in the normal correlation data 232, exceeds a predetermined threshold. As another example, the anomaly detection system 240 might rank the standard deviations of correlations of each pair of parcellations identified in the normal correlation data 232, and determine that the pairs of parcellations with the highest standard deviation or variance are too variable, e.g., the pairs of parcellations in the top 10%, 20%, 30%, or 50%. The anomaly detection system 240 would therefore not identify any of the pairs of parcellations identified to be too variable in the anomaly correlation data 242.

The connectivity data system 200 can provide the anomaly correlation data 242 to one or more downstream systems, e.g., a graphical user interface 250 and/or a machine learning system 260.

The graphical user interface 250 can display data characterizing the one or more pairs of parcellations whose correlations were determined to be anomalous, as identified in the anomaly correlation data 242, to a user. For example, the graphical user interface 250 can display a list of the one or more pairs of parcellations. As another example, the graphical user interface 250 can display an anomaly correlation matrix characterizing the brain of the user. In this specification, an anomaly correlation matrix is a correlation matrix that visually identifies one or more pairs of parcellations, corresponding to respective elements in the anomaly correlation matrix, whose correlation has been determined to be anomalous. This process is discussed in more detail below with respect to FIG. 3 and FIG. 4. As another example, the graphical user interface 250 can display a text summary of the anomaly correlation data 242 and/or a text summary of the corresponding anomaly correlation matrix. As another example, the graphical user interface 250 can display a score calculated according to the anomaly correlation data 242 that characterizes a degree of anomaly in the brain of the patient, e.g., a value between 0 and 1.

In some implementations, the graphical user interface 250 can determine to display a subset of the anomaly correlation data 242 that is determined to be clinically relevant to the user. In this specification, a model output is "clinically relevant" if the model output represents an answer to a question that a trained clinician might ask in clinical practice treating patients, e.g., a question asked by a clinician in order to treat a patient with a specific disease. For example, the graphical user interface 250 might determine one or more particular parcellations that are identified multiple times in the anomaly correlation data, i.e., one or more particular parcellations where such parcellation is a member of multiple different pairs of parcellations whose correlation is anomalous. The graphical user interface can therefore display a portion of the anomaly correlation data 242 related to the particular parcellations, e.g., a subset of the anomaly connectivity matrix. The graphical user interface can also display other data related to the particular parcellations, e.g., a three-dimensional model of tractography data corresponding to particular parcellations.

The machine learning system 260 can include one or more machine learning models that are configured to process the anomaly correlation data 242 and generate a model output that is clinically relevant for a user. For example, a machine learning model can process the anomaly correlation data 242 to generate a prediction for whether the patient has a particular brain disease, e.g., autism, depression, or schizophrenia.

As a particular example, the machine learning system 260 might determine that the patient is at risk for a particular disease according to one or more pairs of parcellations that are known to often be anomalous in brains of patients who have the particular disease. That is, the machine learning system 260 might have determined, through training using brain data of patients with the particular disease, one or more particular pairs of parcellations whose correlations may be indicators of the particular disease. The machine learning system 260 can then determine whether one or more of the particular pairs of parcellations are identified in the anomaly correlation data 242 of the patient, e.g., whether the number of the particular pairs of parcellations identified in the anomaly correlation data 242 exceeds a predetermined threshold. The machine learning system 260 can then recommend to the user to further analyze one or more regions of the brain or disease indicators of the patient.

Referring to FIG. 2B, the connectivity data system 201 is configured to obtain patient brain data 204 characterizing the brain of a patient and process the patient brain data 202 to generate anomaly tractography data 292, which identifies one or more regions of the brain of the patient for which the patient brain data 204 was anomalous. For example, the patient brain data 204 can include one or more of blood-oxygen-level-dependent imaging data, fMRI data, or EEG data captured from the brain of the patient.

The connectivity data system 201 includes a pre-processing system 270, a connectivity data set 280, and an anomaly detection system 290.

The pre-processing system 270 is configured to obtain the patient brain data 204 and process the patient brain data 204 to generate patient tractography data 272 which characterizes neural tracts connecting pairs of parcellations of the multiple parcellation in the brain of the patient.

In some implementations the pre-processing system 270 performs one or more additional pre-processing steps to generate the patient tractography data 272. For example, the pre-processing system 270 can perform one or more pre-processing steps described above with respect to the pre-processing system 210 depicted in FIG. 2A.

The anomaly detection system 290 is configured to obtain the patient tractography data 272 and to process the patient tractography data 272 to generate the anomaly tractography data 292. The anomaly tractography data 292 identifies one or more pairs of parcellations for which the number of connections in the patient tractography data 272 is anomalous.

In some implementations, the anomaly detection system 290 determines the anomaly tractography data 292 by processing the patient tractography data 272 using a machine learning model that is configured to process tractography data and identity one or more pairs of parcellations that are anomalous. For example, the machine learning model can be trained using tractography data obtained from the respective brain of multiple other patients, e.g., training data stored in the connectivity data set 280.

In some other implementations, the anomaly detection system 290 can determine the one or more anomalous pairs of parcellations according to normal tractography data 282 obtained from the connectivity data set 280. In some implementations, the normal tractography data 282 identifies, for each pair of parcellations in the patient tractography data 272, a range of values for the number of tracts connecting the pair of parcellations that is considered "normal." The normal range can be determined by the connectivity data set 280 according to the number of tract connecting the pair of parcellations measured in the respective brain of multiple other patients. For example, the normal tractography data 282 can be determined from brain data captured from hundreds, thousands, or millions of other patients. As a particular example, the normal tractography data 282 might identify, for each pair of parcellations, an average number of tracts between the pair of parcellations and a standard deviation of the number of tracts between the pair of parcellations, as determined from the neural tracts measured in the brains of the other patients.

The anomaly detection system 290 uses the normal tractography data 282 to determine the one or more anomalous pairs of parcellations in the brain of the patient in the anomaly tractography data 292. As a particular example, the anomaly detection system 290 might determine that the number of tracts between a pair of parcellations is anomalous if the number of tracts is outside a range of values defined by the average number of tracts and the standard deviation of the number of tracts connecting the pair of parcellations. For example, the number of tracts connecting a pair of parcellations may be anomalous if it is outside one, two, three, or four standard deviations of the average number of tracts.

As another particular example, the anomaly detection system 290 might determine that a set of two or more pairs of parcellations are anomalous only if the number of tracts between each pair in the set of pairs of parcellations is outside of a normal range of values defined for the set of pairs of parcellations. That is, the anomaly detection system 290 might maintain data that identifies sets of multiple pairs of parcellations that are related to each other, e.g., that are each related to the same disease, such that the anomaly detection system 290 should only determine that an anomaly has occurred if each pair of parcellations in the set of parcellations is anomalous. In this example, normal tractography data 282 might identify a normal range of numbers of tracts corresponding to each pair in the set of pairs of parcellations, where the range of normal values of a first pair in the set depends on the value of one or more other pairs in the set. For example, for any combination of numbers of tracts connecting each of the other pairs in the set, the normal tractography data 282 might define a particular normal range of the number of tracts between the first pair.

In some implementations, the anomaly detection system 290 might identify one or more pairs of parcellations whose "normal" number of connecting tracts, as identified in the normal tractography data 282, are too variable or too unpredictable to draw a conclusion about the corresponding number of tracts identified in the patient tractography data 272. For example, the anomaly detection system 290 might determine that the number of tracts between a pair of parcellations is too variable if the standard deviation or variance of the number of tracts between the pair of parcellations, as identified in the normal tractography data 282, exceeds a predetermined threshold. As another example, the anomaly detection system 290 might rank the standard deviations of the numbers of tracts connecting each pair of parcellations identified in the normal correlation data 282, and determine that the pairs of parcellations with the highest standard deviation are too variable, e.g., the pairs of parcellations in the top 10%, 20%, 30%, or 50%. The anomaly detection system 290 would therefore not identify any of the pairs of parcellations identified to be too variable in the anomaly tractography data 292.

The connectivity data system 201 can provide the anomaly tractography data 292 to one or more downstream systems, e.g., a graphical user interface 250 and/or a machine learning system 260.

The graphical user interface 250 can display data characterizing the one or more pairs of parcellations whose number of connecting tracts were determined to be anomalous, as identified in the anomaly tractography data 292, to a user. For example, the graphical user interface 250 can display a list of the one or more pairs of parcellations. As another example, the graphical user interface 250 can display a model of the tracts of the brain of the patient. As another example, the graphical user interface 250 can display a text summary of the anomaly tractography data 292. As another example, the graphical user interface 250 can display a score calculated according to the anomaly tractography data 292 that characterizes a degree of anomaly in the brain of the patient, e.g., a value between 0 and 1.

In some implementations, the graphical user interface 250 can determine to display a subset of the anomaly tractography data 292 that is determined to be clinically relevant to the user. For example, the graphical user interface 250 might determine one or more particular parcellations that are identified multiple times in the anomaly tractography data, i.e., one or more particular parcellations where such parcellation is a member of multiple different pairs of parcellations whose number of tracts is anomalous. The graphical user interface 250 can therefore display a portion of the anomaly tractography data 292 related to the particular parcellations. The graphical user interface can also display other data related to the particular parcellations, e.g., a portion of an anomaly connectivity matrix corresponding to particular parcellations.

The machine learning system 260 can include one or more machine learning models that are configured to process the anomaly tractography data 292 and generate a model output that is clinically relevant for a user. For example, a machine learning model can process the anomaly tractography data 292 to generate a prediction for whether the patient has a particular brain disease, e.g., autism, depression, or schizophrenia.

As a particular example, the machine learning system 260 might determine that the patient is at risk for a particular disease according to one or more pairs of parcellations that are known to often be anomalous in brains of patients who have the particular disease. That is, the machine learning system 260 might have determined, through training using brain data of patients with the particular disease, one or more particular pairs of parcellations whose number of connecting tracts may be indicators of the particular disease. The machine learning system 260 can then determine whether one or more of the particular pairs of parcellations are identified in the anomaly tractography data 292 of the patient, e.g., whether the number of the particular pairs of parcellations identified in the anomaly tractography data 292 exceeds a predetermined threshold. The machine learning system 260 can then recommend to the user to further analyze one or more regions of the brain or disease indicators of the patient.

Figure 3:
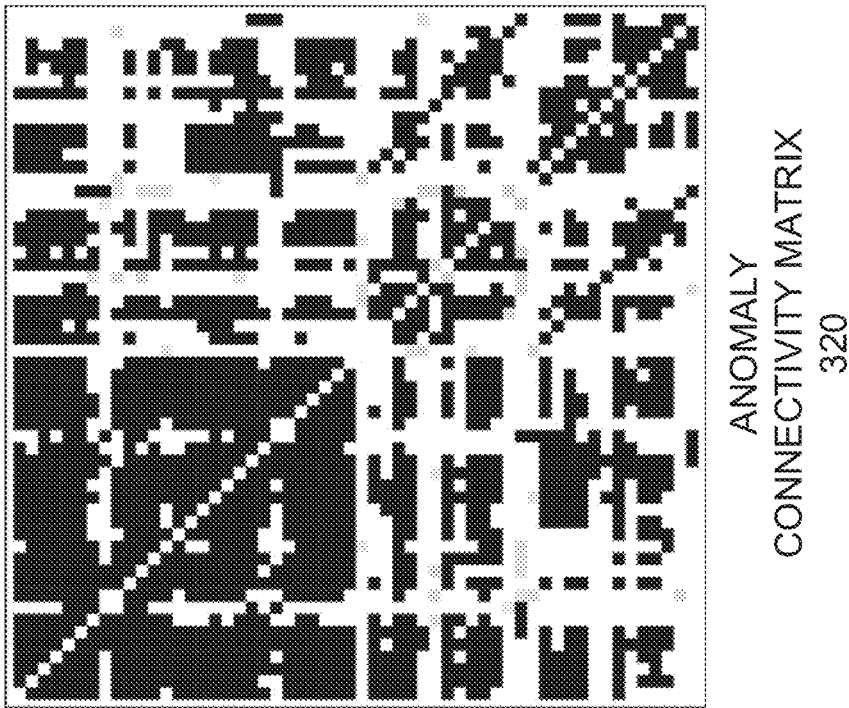
FIG. 3 illustrates example connectivity matrices.
Figure 3:
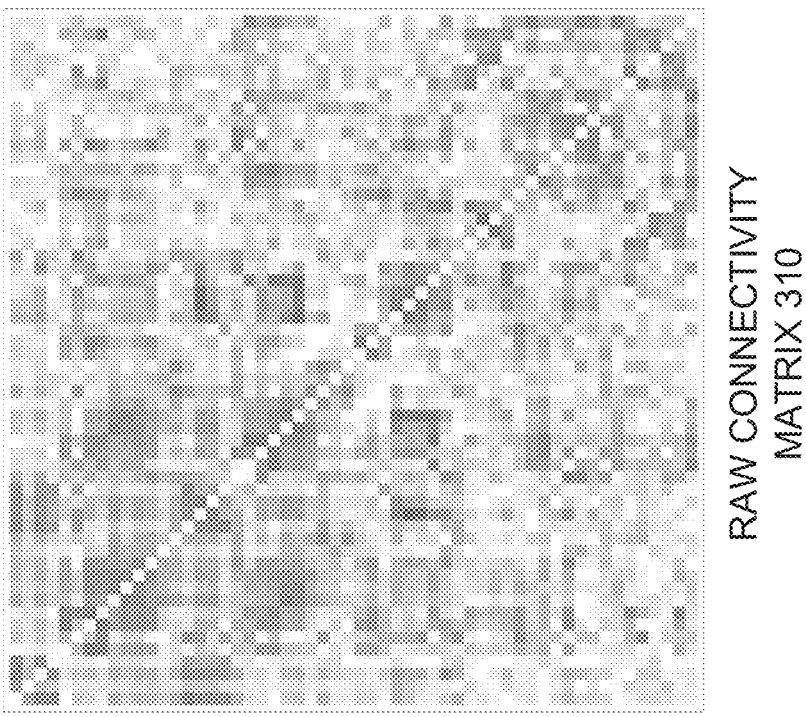

FIG. 3 is an illustration of an example raw connectivity matrix 310 and an example anomaly connectivity matrix 320.

The raw correlation identifies, for each pair of parcellations of multiple parcellations in the brain of a patient, the correlation between brain activity of the first parcellation of the pair of parcellations and the brain activity of the second parcellation of the pair of parcellations. That is, each row and column of the raw connectivity matrix 310 corresponds to a parcellation, and each element has a value identifying the correlation between the parcellation corresponding to the row of the element and the parcellation corresponding to the column of the element. In some implementations, the raw connectivity matrix 310 can include ranges of two different colors, where the first color corresponds to negative correlations and the second color corresponds to positive correlations, and the intensity of a color corresponds to a magnitude of the negative or positive correlation.

It is difficult for a user to inspect a raw connectivity matrix and determine one or more correlations that are anomalous. The user cannot simply identify elements that have a high intensity, because the intensity corresponds to the magnitude of correlation, not the magnitude of anomaly; that is, it may be normal for the correlation between two parcellations to have a large positive or negative correlation.

As described above, an anomaly connectivity matrix identifies one or more pairs of parcellations whose correlation is anomalous. The anomaly matrix 320 visually identifies elements that correspond to pairs of parcellations whose correlations are determined to be too variable (in black), elements that correspond to pairs of parcellations whose correlations have been determine to be "normal" (in white), and elements that correspond to pairs of parcellations whose correlations have been determined to be anomalous (in grayscale). An example anomaly connectivity matrix is discussed in more detail below in reference to FIG. 4.

It is much easier for a user to identify anomalous pairs of parcellations using the anomaly connectivity matrix 320 than the raw connectivity matrix 310. In particular, a user can know to ignore the elements that are black or white, and focus on the elements that are grayscale (or color coded) and therefore indicate anomaly.

Figure 4:
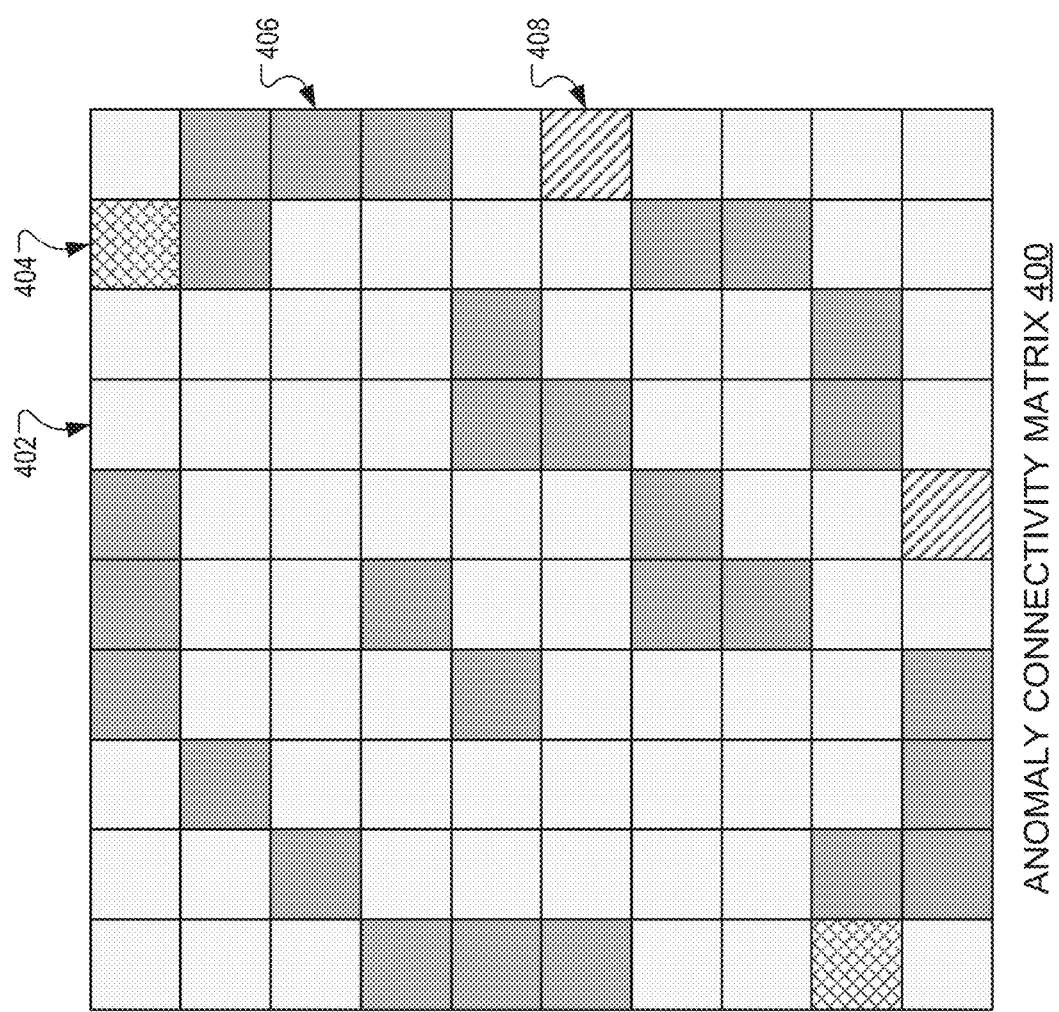
FIG. 4 illustrates an example anomaly connectivity matrix.

FIG. 4 is an illustration of an example anomaly connectivity matrix 400.

The anomaly matrix 400 includes elements, e.g., element 406, that correspond to pairs of parcellations whose correlation has been determined to be too variable to be clinically useful. That is, the correlations of the pair of parcellations determined from brain data gathered from multiple different patients is noisy, e.g., has a relatively large standard deviation compared to correlations of other pairs of parcellations, and therefore is not useful in predicting a mental health status of a patient. As depicted in FIG. 4, these elements have a dark gray color; however, in general the elements can be visually identified in any way, e.g., any color or pattern.

The anomaly matrix 400 includes elements, e.g., element 402, that correspond to pairs of parcellations whose correlation is not too variable, and has been determined to be within a normal range. For example, the correlations may be within a threshold defined by the average correlation and standard deviation of correlations in brain data of multiple different patients. As depicted in FIG. 4, these elements have a light gray color; however, in general the elements can be visually identified in any way, e.g., any color or pattern.

The anomaly matrix 400 includes elements, e.g., element 404, that correspond to pairs of parcellations whose correlation has been determined to be anomalous because it is higher than the normal range. As depicted in FIG. 4, these elements have a checkered pattern; however, in general the elements can be visually identified in any way, e.g., any pattern or range of colors. As a particular example, the elements identifying a higher correlation than normal can be identified by a range of colors whose intensity corresponds to the degree to which the correlation is higher than normal.

The anomaly matrix 400 includes elements, e.g., element 408, that correspond to pairs of parcellations whose correlation has been determined to be anomalous because it is lower than the normal range. As depicted in FIG. 4, these elements have a striped pattern; however, in general the elements can be visually identified in any way, e.g., any pattern or range of colors. As a particular example, the elements identifying a lower correlation than normal can be identified by a range of colors whose intensity corresponds to the degree to which the correlation is lower than normal.

Figure 5:
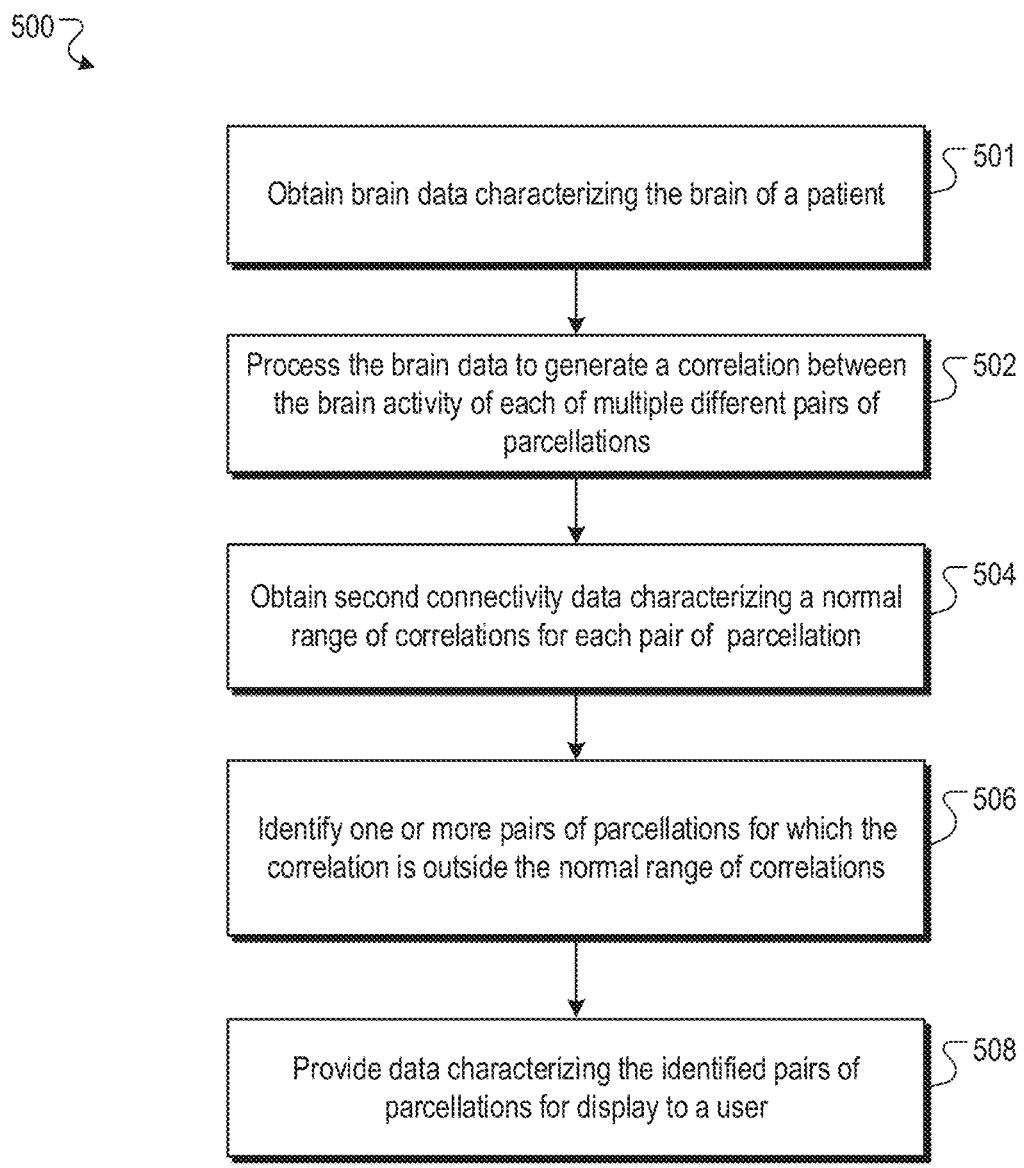
FIG. 5 is a flowchart of an example process for determining an anomalous subset of brain data.

FIG. 5 is a flowchart of an example process 500 for determining an anomalous subset of brain data. The process 500 can be implemented by one or more computer programs installed on one or more computers and programmed in accordance with this specification. For example, the process 500 can be performed by the computer server module depicted in FIG. 1A. For convenience, the process 500 will be described as being performed by a system of one or more computers.

The system obtains brain data captured by one or more sensors characterizing the brain of a patient (step 501). The brain data can include one or more of blood-oxygen-level-dependent imaging data, fMRI data, EEG data, or tractography data.

For each of multiple pairs of parcellations formed from a set of parcellations, the system processes the brain data to generate a correlation in the brain of the patient between the brain activity of the first parcellation in the pair of parcellations and the brain activity of the second parcellation in the pair of parcellations (step 502).

In some implementations, the brain data can include, for each of multiple voxels in the brain of the patient, a time series data sequence characterizing the brain activity at the voxel. In these implementations, the system can assign, for each voxel in the brain of the patient, the voxel to a particular parcellation of the plurality of parcellations, and combine, for each parcellation, the time series data sequences corresponding to the voxels assigned to the parcellation to generate a respective parcellation time series data sequence.

The system obtains second connectivity data that characterizes, for each first parcellation and second parcellation of the set of parcellations, a normal range of correlations between the brain activity of the first parcellation and the second parcellation (step 504). The second connectivity data can be generated from connectivity data corresponding to multiple other patients.

The second connectivity data can include, for each pair of parcellations, data characterizing i) a measure of central tendency of the correlation between the brain activity of the pair of parcellations, and ii) a measure of variance of the correlation between the brain activity of the pair of parcellations. As a particular example, the normal range between the brain activity of a pair of parcellations can be defined by i) a first value that specifies a maximum correlation and ii) a second value that specifies a minimum correlation. The first value and the second value can be linear combinations of the corresponding measure of central tendency and the corresponding measure of variance.

The system identifies one or more of the pairs of parcellations for which the correlation between brain activity of the first parcellation and the second parcellation of the pair is outside of the corresponding normal range of correlations specified in the second connectivity data (step 506). For example, the system can identify one or more pairs of parcellations for which i) the correlation between brain activity of the pair of parcellations in the brain of the patient specified in the first connectivity data is outside of the corresponding normal range of correlations specified in the second connectivity data, and ii) the measure of variance corresponding to the pair of parcellations in the second connectivity data is below a threshold value.

The system provides data characterizing the one or more identified pairs of parcellations for display to a user on a graphical interface (step 508). For example, the system can display an anomaly connectivity matrix generated from the identified pairs of parcellations to the user.

In some implementations, the system can determine an area of the brain of the patient that includes one or more particular parcellations that are in the one or more identified pairs of parcellations, and display data corresponding to the determined area of the brain of the patient.

In some implementations, the system can provide data characterizing the one or more identified pairs of parcellations as input to a machine learning model, e.g., a machine learning model that is configured to predict whether the patient has a particular disease.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a Method Comprising:
obtaining brain data captured by one or more sensors characterizing brain activity of a patient at a plurality of time points;
for each of a plurality of pairs of parcellations formed from a set of parcellations where each pair comprises a first parcellation and a second parcellation, processing the brain data to generate a correlation between the brain activity of the first parcellation and the brain activity of the second parcellation in the brain of the patient;
obtaining second connectivity data that characterizes, for each of the plurality of pairs of parcellations, a normal range of correlations between the brain activity of the first parcellation and the second parcellation of the pair of parcellations;
identifying one or more of the plurality of pairs of parcellations for which the correlation between brain activity of the first parcellation and the second parcellation of the pair is outside of the corresponding normal range of correlations specified in the second connectivity data; and
providing data characterizing the one or more identified pairs of parcellations for display to a user on a graphical interface.

Embodiment 2 is the method of embodiment 1, wherein:
the brain data comprises, for each voxel of a plurality of voxels in the brain of the patient, a time series data sequence characterizing the brain activity at the voxel at the plurality of time points; and
processing the brain data to generate first connectivity data comprises:
assigning, for each voxel in the brain of the patient, the voxel to a particular parcellation of the plurality of parcellations;
combining, for each parcellation in the plurality of parcellations, the time series data sequences corresponding to the voxels assigned to the parcellation to generate a respective parcellation time series data sequence.

Embodiment 3 is the method of any one of embodiments 1 or 2, wherein the brain data comprises one or more of:
blood-oxygen-level-dependent imaging data,
fMRI data,
EEG data, or
tractography data.

Embodiment 4 is the method of any one of embodiments 1-3, wherein:
the second connectivity data is generated from a plurality of sets of third connectivity data corresponding to respective other patients, wherein each set of third connectivity data characterizes, for each first parcellation and second parcellation of the plurality of parcellations, a correlation between the brain activity of the first parcellation and the brain activity of the second parcellation in the brain of the corresponding other patient; and
the second connectivity data comprises, for each pair of parcellations in the plurality of parcellations, data characterizing i) a measure of central tendency of the correlation between the brain activity of the pair of parcellations, and ii) a measure of variance of the correlation between the brain activity of the pair of parcellations, wherein the measures of central tendency and the measure of variance have been computed using the plurality of sets of third connectivity data.

Embodiment 5 is the method of embodiment 4, wherein, for each pair of parcellations in the plurality of parcellations, the normal range of correlations between the brain activity of the pair of parcellations is defined by i) a first value that specifies a maximum correlation and ii) a second value that specifies a minimum correlation, wherein the first value and the second value are linear combinations of the corresponding measure of central tendency and the corresponding measure of variance.

Embodiment 6 is the method of any one of embodiments 4 or 5, wherein identifying one or more pairs of parcellations comprises identifying one or more pairs of parcellations for which i) the correlation between brain activity of the pair of parcellations in the brain of the patient specified in the first connectivity data is outside of the corresponding normal range of correlations specified in the second connectivity data, and ii) the measure of variance corresponding to the pair of parcellations in the second connectivity data is below a threshold value.

Embodiment 7 is the method of embodiment 6, wherein the threshold value is equal to a particular measure of variance corresponding to a particular pair of parcellations in the second connectivity data.

Embodiment 8 is the method of any one of embodiments 1-7, wherein providing the data characterizing the one or more identified pairs of parcellations for display to the user comprises providing data characterizing a connectivity matrix comprising a plurality of cells, wherein:

each cell corresponds to a pair of parcellations of the plurality of parcellations and each cell has a corresponding indication characterizing a difference between i) the correlation between the brain activity of the respective pair of parcellations in the brain of the patient, and ii) the normal range of correlations between the brain activity of the respective pair of parcellations, wherein:

a first indication indicates that the correlation between the brain activity of the respective pair of parcellations in the brain of the patient is higher than the normal range of correlations, a second indication indicates that the correlation between the brain activity of the respective pair of parcellations in the brain of the patient is lower than the normal range of correlations, and a third indication indicates that the correlation between the brain activity of the respective pair of parcellations in the brain of the patient is within the normal range of correlations.

Embodiment 9 is the method of embodiment 8, wherein:

the second connectivity data comprises, for each pair of parcellations, data characterizing a measure of variance of the correlation between the brain activity of the pair of parcellations; and a fourth color or set of colors indicates that the measure of variance corresponding to the respective pair of parcellations is higher than a threshold value.

Embodiment 10 is the method of any one of embodiments 1-9, wherein providing data characterizing the one or more identified pairs of parcellations for display to a user comprises:

determining an area of the brain of the patient that includes one or more particular parcellations that are in the one or more identified pairs of parcellations; and displaying data corresponding to the determined area of the brain of the patient.

Embodiment 11 is the method of any one of embodiments 1-10, further comprising providing data characterizing the one or more identified pairs of parcellations as input to a machine learning model.

Embodiment 12 is the method of any one of embodiments 1-11, wherein the data characterizing the one or more identified pairs of parcellations comprises, for each of the one or more identified pairs, an indication of a degree to which the correlation is outside of the corresponding normal range of correlations.

Embodiment 13 is the method of embodiment 12, wherein the data characterizing the one or more identified pairs of parcellations comprises, for each of the one or more identified pairs, a simultaneous display of a plurality of indications of the degree to which each correlation is outside the normal range.

Embodiment 14 is a system comprising one or more computers and one or more storage devices storing instructions that are operable, when executed by the one or more computers, to cause the one or more computers to perform the method of any one of embodiments 1-13.

Embodiment 15 is a computer storage medium encoded with a computer program, the program comprising instructions that are operable, when executed by data processing apparatus, to cause the data processing apparatus to perform the method of any one of embodiments 1-13.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A computer-implemented method comprising:

obtaining first data generated from brain data captured by one or more sensors and characterizing brain activity of a patient, the first data comprising, for each of a plurality of pairs of parcellations formed from a set of parcellations where each pair comprises a first parcellation and a second parcellation, a correlation between the brain activity of the first parcellation and the brain activity of the second parcellation in the brain of the patient, wherein the plurality of pairs of parcellations comprises at least 45 pairs of parcellations;

obtaining second data that characterizes, for each of the plurality of pairs of parcellations, a normal range of correlations values for the brain activity of the first parcellation and the brain activity of the second parcellation of the pair of parcellations;

identifying, using an anomaly detection system, one or more of the plurality of pairs of parcellations for which the correlation between the brain activity of the first parcellation and the brain activity of the second parcellation of the pair of parcellations is outside of the corresponding normal range of correlations specified in the second data to generate comparison data characterizing the one or more identified pairs of parcellations; and providing the comparison data in the form of an anomaly matrix having a plurality of anomaly matrix cells for display to a user on a graphical interface, the comparison data characterizing the plurality of anomaly matrix cells, wherein:

each cell corresponds to a respective pair of parcellations of the plurality of parcellations, and for each of the one or more identified pairs of parcellations, the anomaly matrix comprises a corresponding cell having a respective indication characterizing a difference between (i) the correlation corresponding to the pair of parcellations specified in the first data and (ii) the normal range of correlations corresponding to the pair of parcellations specified in the second data.

2. The method of claim 1, wherein:
the brain data comprises, for each voxel of a plurality of voxels in the brain of the patient, a time series data sequence characterizing the brain activity at the voxel at the plurality of time points; and
the first data has been generated from the brain data by performing operations comprising:
   assigning, for each voxel in the brain of the patient, the voxel to a particular parcellation of the plurality of parcellations;
   combining, for each parcellation in the plurality of parcellations, the time series data sequences corresponding to the voxels assigned to the parcellation to generate a respective parcellation time series data sequence.

3. The method of claim 1, wherein the brain data comprises one or more of:
blood-oxygen-level-dependent imaging data,
fMRI data,
EEG data, or
tractography data.

4. The method of claim 1, wherein:
the second data is generated from a plurality of sets of third data corresponding to respective other patients, wherein each set of third data characterizes, for each first parcellation and second parcellation of the plurality of parcellations, a correlation between the brain activity of the first parcellation and the brain activity of the second parcellation in the brain of the corresponding other patient; and
the second data comprises, for each pair of parcellations of the plurality of parcellations, data characterizing i) a measure of central tendency of the correlation between the brain activity of the pair of parcellations, and ii) a measure of variance of the correlation between the brain activity of the pair of parcellations, wherein the measures of central tendency and the measure of variance have been computed using the plurality of sets of third data.

5. The method of claim 4, wherein, for each pair of parcellations in the plurality of parcellations, the normal range of correlations between the brain activity of the pair of parcellations is defined by i) a first value that specifies a maximum correlation and ii) a second value that specifies a minimum correlation, wherein the first value and the second value are linear combinations of the corresponding measure of central tendency and the corresponding measure of variance.

6. The method of claim 4, wherein identifying one or more pairs of parcellations comprises identifying one or more pairs of parcellations for which i) the correlation between brain activity of the pair of parcellations in the brain of the patient specified in the first data is outside of the corresponding normal range of correlations specified in the second data, and ii) the measure of variance corresponding to the pair of parcellations in the second data is below a threshold value.

7. The method of claim 6, wherein the threshold value is equal to a particular measure of variance corresponding to a particular pair of parcellations in the second data.

8. The method of claim 1, wherein each cell of the anomaly matrix has one of:
a first indication indicates that the correlation between the brain activity of the respective pair of parcellations in the brain of the patient is higher than the normal range of correlations,
a second indication indicates that the correlation between the brain activity of the respective pair of parcellations in the brain of the patient is lower than the normal range of correlations, and
a third indication indicates that the correlation between the brain activity of the respective pair of parcellations in the brain of the patient is within the normal range of correlations.

9. The method of claim 8, wherein:
the second data comprises, for each pair of parcellations, data characterizing a measure of variance of the correlation between the brain activity of the pair of parcellations; and
a fourth indication indicates that the measure of variance corresponding to the respective pair of parcellations is higher than a threshold value.

10. The method of claim 1, wherein providing the comparison data for display to a user comprises:
determining an area of the brain of the patient that includes one or more particular parcellations that are in the one or more identified pairs of parcellations; and
providing data for display corresponding to the determined area of the brain of the patient.

11. The method of claim 1, further comprising providing data characterizing the one or more identified pairs of parcellations as input to a machine learning model.

12. The method of claim 1, wherein, for each of the one or more identified pairs of parcellations, the corresponding cell of the anomaly matrix has an indication of a degree to which the correlation is outside of the corresponding normal range of correlations.

13. A system comprising one or more computers and one or more storage devices storing instructions that are operable, when executed by the one or more computers, to cause the one or more computers to perform operations comprising:
obtaining first data generated from brain data captured by one or more sensors and characterizing brain activity of a patient, the first data comprising, for each of a plurality of pairs of parcellations formed from a set of parcellations where each pair comprises a first parcellation and a second parcellation, a correlation between the brain activity of the first parcellation and the brain activity of the second parcellation in the brain of the patient, wherein the plurality of pairs of parcellations comprises at least 45 pairs of parcellations;

obtaining second data that characterizes, for each of the plurality of pairs of parcellations, a normal range of correlations values for the brain activity of the first parcellation and the brain activity of the second parcellation of the pair of parcellations;

identifying, using an anomaly detection system, one or more of the plurality of pairs of parcellations for which the correlation between the brain activity of the first parcellation and the brain activity of the second parcellation of the pair of parcellations is outside of the corresponding normal range of correlations specified in the second data to generate comparison data characterizing the one or more identified pairs of parcellations; and providing the comparison data in the form of an anomaly matrix having a plurality of anomaly matrix cells for display to a user on a graphical interface, the comparison data characterizing the plurality of anomaly matrix cells, wherein:

each cell corresponds to a respective pair of parcellations of the plurality of parcellations, and for each of the one or more identified pairs of parcellations, the anomaly matrix comprises a corresponding cell having a respective indication characterizing a difference between (i) the correlation corresponding to the pair of parcellations specified in the first data and (ii) the normal range of correlations corresponding to the pair of parcellations specified in the second data.

14. A computer-implemented method comprising:

obtaining first data generated from brain data captured by one or more sensors and characterizing brain activity of a patient, the first data comprising, for each of a plurality of pairs of parcellations formed from a set of parcellations where each pair comprises a first parcellation and a second parcellation, a tractography measure representing a strength or number of neural tracts connecting the first parcellation and the second parcellation in the brain of the patient, wherein the plurality of pairs of parcellations comprises at least 45 pairs of parcellations;

obtaining second data that characterizes, for each of the plurality of pairs of parcellations, a normal range of tractography measures representing the strength or number of neural tracts connecting the pair of parcellations;

identifying, using an anomaly detection system, one or more of the plurality of pairs of parcellations for which the tractography measure corresponding to the pair of parcellations specified in the first data is outside of the corresponding normal range of tractography measures specified in the second data to generate comparison data characterizing the one or more identified pairs of parcellations; and providing the comparison data in the form of an anomaly matrix having a plurality of anomaly matrix cells for display to a user on a graphical interface, the comparison data characterizing the plurality of anomaly matrix cells wherein, for each of the one or more identified pairs of parcellations, a respective indication characterizes a difference between (i) the tractography measure corresponding to the pair of parcellations specified in the first data and (ii) the normal range of tractography measures corresponding to the pair of parcellations specified in the second data.

15. The method of claim 14, wherein:

the brain data comprises, for each voxel of a plurality of voxels in the brain of the patient, a time series data sequence characterizing the brain activity at the voxel at the plurality of time points; and the first data has been generated from the brain data by performing operations comprising:
assigning, for each voxel in the brain of the patient, the voxel to a particular parcellation of the plurality of parcellations;
combining, for each parcellation in the plurality of parcellations, the time series data sequences corresponding to the voxels assigned to the parcellation to generate a respective parcellation time series data sequence.

16. The method of claim 14, wherein:

the second data is generated from a plurality of sets of third data corresponding to respective other patients, wherein each set of third data characterizes, for each first parcellation and second parcellation of the plurality of parcellations, a tractography measure representing a strength or number of neural tracts connecting the first parcellation and the second parcellation in the brain of the other patient; and the second data comprises, for each pair of parcellations of the plurality of parcellations, data characterizing i) a measure of central tendency of the tractography measure of the pair of parcellations, and ii) a measure of variance of the tractography measure of the pair of parcellations, wherein the measures of central tendency and the measure of variance have been computed using the plurality of sets of third data.

17. The method of claim 16, wherein, for each pair of parcellations in the plurality of parcellations, the normal range of tractography measures representing the strength or number of neural tracts connecting the pair of parcellations is defined by i) a first value that specifies a maximum tractography measure and ii) a second value that specifies a minimum tractography measure, wherein the first value and the second value are linear combinations of the corresponding measure of central tendency and the corresponding measure of variance.

18. The method of claim 16, wherein identifying one or more pairs of parcellations comprises identifying one or more pairs of parcellations for which i) the tractography measure corresponding to the pair of parcellations specified in the first data is outside of the corresponding normal range of tractography measures specified in the second data, and ii) the measure of variance corresponding to the pair of parcellations in the second data is below a threshold value.

19. The method of claim 14, wherein providing the comparison data for display to a user comprises:
determining an area of the brain of the patient that includes one or more particular parcellations that are in the one or more identified pairs of parcellations; and
providing data for display corresponding to the determined area of the brain of the patient.

20. The method of claim 14, further comprising providing data characterizing the one or more identified pairs of parcellations as input to a machine learning model.

21. The method of claim 14, wherein providing the comparison data for display to a user comprises providing data for display characterizing a model of the neural tracts in the brain of the patient.

* * * * *